(12) United States Patent
Barralon (10) Patent No.: US 10,376,222 B2
(45) Date of Patent: Aug. 13, 2019

(54) METHOD AND SYSTEM FOR FUNCTIONAL BALANCE ASSESSMENT

(71) Applicant: Fundacion Tecnalia Research & Innovation, San Sebastian-Guipuzcoa (ES)

(72) Inventor: Pierre Barralon, San Sebastian-Guipuzcoa (ES)

(*) Notice: Subject to any disclaimer, the term of this patent is extended or adjusted under 35 U.S.C. 154(b) by 505 days.

(21) Appl. No.: 14/934,531

(22) Filed: Nov. 6, 2015

(65) Prior Publication Data
US 2016/0128642 A1 May 12, 2016

(30) Foreign Application Priority Data
Nov. 6, 2014 (EP) .................................... 14382441

(51) Int. Cl.
*A61B 5/00* (2006.01)
*A61B 5/103* (2006.01)
*A61B 5/11* (2006.01)

(52) U.S. Cl.
CPC .......... *A61B 5/7278* (2013.01); *A61B 5/1036* (2013.01); *A61B 5/4023* (2013.01); *A61B 5/6823* (2013.01); *A61B 5/6887* (2013.01); *A61B 5/1038* (2013.01); *A61B 5/112* (2013.01); *A61B 5/1127* (2013.01); *A61B 2562/0219* (2013.01); *A61B 2562/0247* (2013.01); *A63B 2220/806* (2013.01)

(58) Field of Classification Search
CPC ...... A61B 5/1036–1038; A61B 5/4023; A61B 5/112; A61B 5/1127; A61B 5/7278; A61B 5/6823; A63B 2220/806
See application file for complete search history.

(56) References Cited

U.S. PATENT DOCUMENTS

| | | | |
|---|---|---|---|
| 5,744,953 A * | 4/1998 | Hansen | A61B 5/1036 324/207.17 |
| 6,176,837 B1 * | 1/2001 | Foxlin | G01C 21/165 128/897 |
| 8,845,556 B1 * | 9/2014 | Schickler | A61B 5/1036 340/573.7 |

(Continued)

*Primary Examiner* — Devin B Henson
(74) *Attorney, Agent, or Firm* — Eugenio J. Torres-Oyola; Victor M. Rodriguez-Reyes; Rafael Rodriguez-Muriel (57) ABSTRACT

A system comprising: at least one platform configured for, in use, having a person on it, said platform comprising a plurality of sensors configured for capturing information of forces/pressures applied by the feet of the person or of the position of the person's feet; means for, from said captured information, respectively extracting either a center of pressure or the position of the feet; at least one reference signal disposed at a known location with respect to said platform; at least one sensor which, in use, is connected to the body of the person situated on said platform, the sensor being configured for capturing said at least one reference signal; processing means for extracting information from said at least one captured reference signal and for estimating the position and/or orientation of said at least one sensor; processing means for estimating the position and/or orientation of the body of said person; processing means for calculating a stability index from said position and/or orientation of the body of said person and from said extracted feet position or center of pressure.

13 Claims, 9 Drawing Sheets

(56) References Cited

U.S. PATENT DOCUMENTS

| | | | |
|---|---|---|---|
| 8,920,344 B2* | 12/2014 | Ernst | A61B 5/1116 |
| | | | 600/595 |
| 9,526,946 B1* | 12/2016 | Zets | A63B 24/00 |
| 9,801,568 B2* | 10/2017 | Ziaie | A61B 5/112 |
| 2006/0022833 A1* | 2/2006 | Ferguson | A61B 5/1124 |
| | | | 340/573.1 |
| 2007/0275830 A1* | 11/2007 | Lee | A61B 5/1038 |
| | | | 482/54 |
| 2010/0035727 A1* | 2/2010 | Brunner | A61B 5/1038 |
| | | | 482/8 |
| 2012/0159290 A1* | 6/2012 | Pulsipher | G06K 9/00369 |
| | | | 714/819 |
| 2013/0296740 A1* | 11/2013 | Greenawalt | A61B 5/1036 |
| | | | 600/592 |
| 2014/0024972 A1* | 1/2014 | Greene | A61B 5/1038 |
| | | | 600/595 |
| 2014/0276130 A1* | 9/2014 | Mirelman | A61B 5/744 |
| | | | 600/483 |
| 2015/0173652 A1* | 6/2015 | Brunner | A61B 5/112 |
| | | | 482/7 |
| 2015/0208975 A1* | 7/2015 | Ghajar | A61B 5/16 |
| | | | 600/595 |
| 2016/0007902 A1* | 1/2016 | Hewson | A61B 5/11 |
| | | | 600/592 |
| 2016/0081594 A1* | 3/2016 | Gaddipati | A61B 5/1113 |
| | | | 600/595 |

\* cited by examiner

METHOD AND SYSTEM FOR FUNCTIONAL BALANCE ASSESSMENT

CROSS-REFERENCE TO RELATED APPLICATIONS

This application claims priority from European Application No. EP14382441 filed on Nov. 6, 2014.

FIELD OF THE INVENTION

The present invention relates to the field of kinematic and kinetic non-invasive sensing technologies and, more particularly, to sensing technologies for estimating, monitoring and/or training the relative position, motion and/or resultant forces of different human body parts. This invention pertains to methods and devices for assessing, training, and aiding in the rehabilitation of postural balance including those providing feedback of postural information to the subject.

Among others, the invention is applicable to certain diagnostic devices, such as force platforms, stabilometric and/or baropodometric platforms or sensorized walkways; to certain training devices, such as dynamic balance platforms; and to sporting goods, such as surfboards, snowboards, etc.

BACKGROUND OF THE INVENTION

Clinical assessment scales in relation to motion and balance have been developed and are currently daily used by clinicians. Evaluation criteria are very (clinically) relevant but, at the same time, they are subjective and consequently practitioner-dependent. Therefore, there is a need to have quantitative assessment tools.

During the last 30 years, instrumental tools have been suggested to evaluate quantitatively postural balance parameters. It has been observed that directly measuring stability is impossible because stability is not a magnitude, but merely an aptitude, enabling the body to return close to its position of equilibrium whenever strays from it. Nonetheless, Human stability has characteristics that can be measured. The most complete approach to describe and quantify human stability is the angular momentum approach [Herr 2008]. It however requires the measurements of the full body dynamics (both all body segments kinematics and external forces) or full body kinematic knowing inertia properties of all body segments. Such equipment and time consuming procedures are only used for research purposes. Indeed, stabilometric platform, which measures Center of Pressure (CoP), is currently the device the most used by professionals.

Apart from these two approaches which correspond to the two ends of the spectrum, namely devices based only on CoP measures and devices based on full body dynamics, there are intermediate devices that can provide complete enough information and still meet professional requirements (cost, diagnostics time). Aligned with this approach several studies have analyzed the relationship between subsets of data (Center of Pressure (CoP) alone [Spaepen 1977, Winter 1995], Center of Mass (CoM) alone [Hof 2005], CoP-CoM [Hahn 2004], CoM-Foot placement [Pai 1997, Slobounov 1977]) and their relationship with clinical scales (Timed Get-up-and-go, Berg Balance Scale, Tinetti Balance Scale, One Leg Stance). Scientific evidences support the paradigm that a joint analysis of Center of Mass (CoM)-Center of Pressure (CoP) and/or Center of Mass (CoM)-Foot placement reflects human functional stability.

Several proposals have been made for assessing or analyzing the equilibrium state of a person. There are conventional proposals based on sensors which, either attached to the body of the user or integrated in a mobile terminal carried by the user, provide information about his/her stability. For example, United States patent application US2011092860A1 discloses a system for clinical assessment of movement disorders which comprises a plurality of wearable sensors including accelerometers, gyroscopes, magnetometers, optical sensors, and goniometers to record kinematics data obtained from a patient. In turn, European patent application EP2578151A1 describes a mobile terminal device for acquiring walking posture loci. It has an angular velocity sensor, an acceleration sensor and a storage unit for storing a walking posture reference locu. International patent application WO2004103176A1 discloses a system for diagnosing balance based on a motion sensor wearable on a user Besides, European patent application EP1527734A1 discloses an apparatus for analysing an equilibrium state based on acceleration information detecting means attached to the trunk of the human body, motion information storing means and equilibrium state analysing means.

Other well-known proposals comprise image capturing devices for helping to estimate the balance state of the person. For example, International patent application WO2007135462A1 discloses a system and method for monitoring a person's balance which comprises a unit bearing one indicium and an image capture device. One of both is attached to the person at his/her center of balance. Movement of the indicium is recorded with reference to the subject's center of balance.

On the other hand, there are systems for monitoring the movements of a person based on pressure changes. For example, United States patent application US201117573A1 describes a method and system for measuring and analysing human body balance signals caused by pressure change. From these signals, the human body center of gravity offset is evaluated to obtain the CoP (center of pressure) offset and CoP offset velocity. Also U.S. Pat. No. 8,011,229B2 discloses a method for determining postural stability of a person by acquiring a plurality of pressure data points over a period of time from several pressure sensors placed, for example, all the soles of the person's shoes.

These well-known methods and systems normally measure the Center of Pressure (CoP) or the plantar pressure distribution, which are compensatory mechanisms (at the level of the feet) to maintain postural stability. However, they are unable to identify the causes of instability. Besides, it is not possible to establish a relationship between a center of pressure and a body position, taking into account that the person under observation tends to move due to his/her stability problems. As a consequence, there is a need to have instrumental measures closer to functional criteria.

Therefore, even if technologies exist which enable to quantitatively measure functional stability, there is a need for an integrated technology that can be largely deployed among clinicians and/or balance professionals.

SUMMARY OF THE INVENTION

The present invention describes systems and methods for assessing human postural stability based on the measurements and analysis of the simultaneous and relative evolution of at least two parameters of Human kinematics and/or kinetics. As will be apparent from the description of exemplary embodiments, these two parameters can be the relative position of the feet (e.g. Base of Support) and the whole human center of mass (CoM) of a person, or the relative position of human center of mass (CoM) with respect to the Center of Pressure (CoP), or the relative position of human center of mass (CoM) with respect to both BoS and CoP. Based on the simultaneous measurements of this complementary information, various features are calculated or estimated to be merged and provide a Stability Index (SI) value.

It is an object of the present invention to provide a system comprising: at least one platform configured for, in use, having a person on it, wherein the platform comprises a plurality of sensors configured for capturing information of forces/pressures applied by the feet of the person or of the position of the person's feet; means for, from the captured information, respectively extracting either a center of pressure or the position of the feet; at least one reference signal disposed at a known location with respect to the platform; at least one sensor which, in use, is connected to the body of the person situated on the platform, the sensor being configured for capturing the at least one reference signal; processing means for extracting information from the at least one captured reference signal and for estimating the position and/or orientation of the at least one sensor; processing means for estimating the position and/or orientation of the body of the person; processing means for calculating a stability index from the position and/or orientation of the body of the person and from the extracted feet position or center of pressure.

Preferably, the at least one sensor connected to the body of the person situated on the platform comprises a camera and the at least one reference signal disposed at a known location with respect to the platform is a visual pattern. More preferably, the at least one visual pattern is an infrared visual pattern and the at least one camera is configured to capture images in the infrared range of light.

Preferably, the platform is a plantar pressure distribution system or a force platform). In a preferred embodiment, the stability index is a function of the position and orientation of the at least one sensor connected to the body of the person situated on the platform and at least one of the following inputs: a base of support, a center of pressure, a ground reaction force and one or more features derived from those inputs. In a preferred embodiment, the at least one sensor connected to the body of the person situated on the platform is adapted to be connected to the trunk of the person. In a particular embodiment, the at least one sensor connected to the body of the person situated on the platform comprises at least one acceleration transducer for measuring the sensor acceleration or at least one angular velocity transducer for measuring the sensor angular velocity. The at least one reference signal can be placed either on or outside the platform. In a particular embodiment, the orientation of the at least one sensor connected to the body is actuated by at least one servo motor.

It is another object of the present invention to provide a method comprising the steps of: at a plurality of sensors located at a platform on which a person is situated, capturing information of the pressure applied by the feet of the person or of the position of the person's feet; from the captured information, respectively extracting either a center of pressure or a feet position; by means of at least one sensor connected to the body of the person situated on the platform, capturing at least one reference signal disposed at a known location with respect to the platform; extracting information from the at least one captured reference signal; estimating the position and/or orientation of the at least one sensor; estimating the position and/or orientation of the body of the person; and calculating a stability index from the position and/or orientation of the body of the person and from the extracted feet position or center of pressure.

Preferably, the stage of estimating the position and/or orientation of the body of the person is done as follows: extracting a point of interest from the at least one image; estimating the relative position of the sensor with respect to the visual pattern and the orientation of the sensor; and estimating the center of mass of the person from the relative position and orientation of the sensor.

In a particular embodiment, the sensor acceleration and/or the sensor angular velocity and/or the magnetic orientation of the sensor is measured. In this case, the stage of estimating the position and/or orientation of the at least one sensor is refined as follows: acquiring the acceleration and/or angular velocity and/or magnetic orientation of the sensor; estimating the sensor relative translation and orientation; and refining the estimation of the sensor position and orientation by combining the initial estimation with the additional information available.

Additional advantages and features of the invention will become apparent from the detail description that follows and will be particularly pointed out in the appended claims.

DETAILED DESCRIPTION OF THE INVENTION

Systems and methods are described for assessing human postural stability based on the measurements and analysis of the simultaneous and relative evolution of at least two parameters of human kinematics and/or kinetics. The same apparatus can be used for training human postural stability. In one particular embodiment, the at least two parameters are the relative position of the feet (e.g. Base of Support) and the whole human center of mass (CoM) of a person. In another particular embodiment, the at least two parameters are the relative position of human center of mass (CoM) with respect to the Center of Pressure (CoP). In another particular embodiment, the parameters are the relative position of human center of mass (CoM) with respect to both BoS and CoP.

Based on the simultaneous measurements of this complementary information, various features are calculated or estimated to be merged and provide a Stability Index (SI) value.

Figure 5:
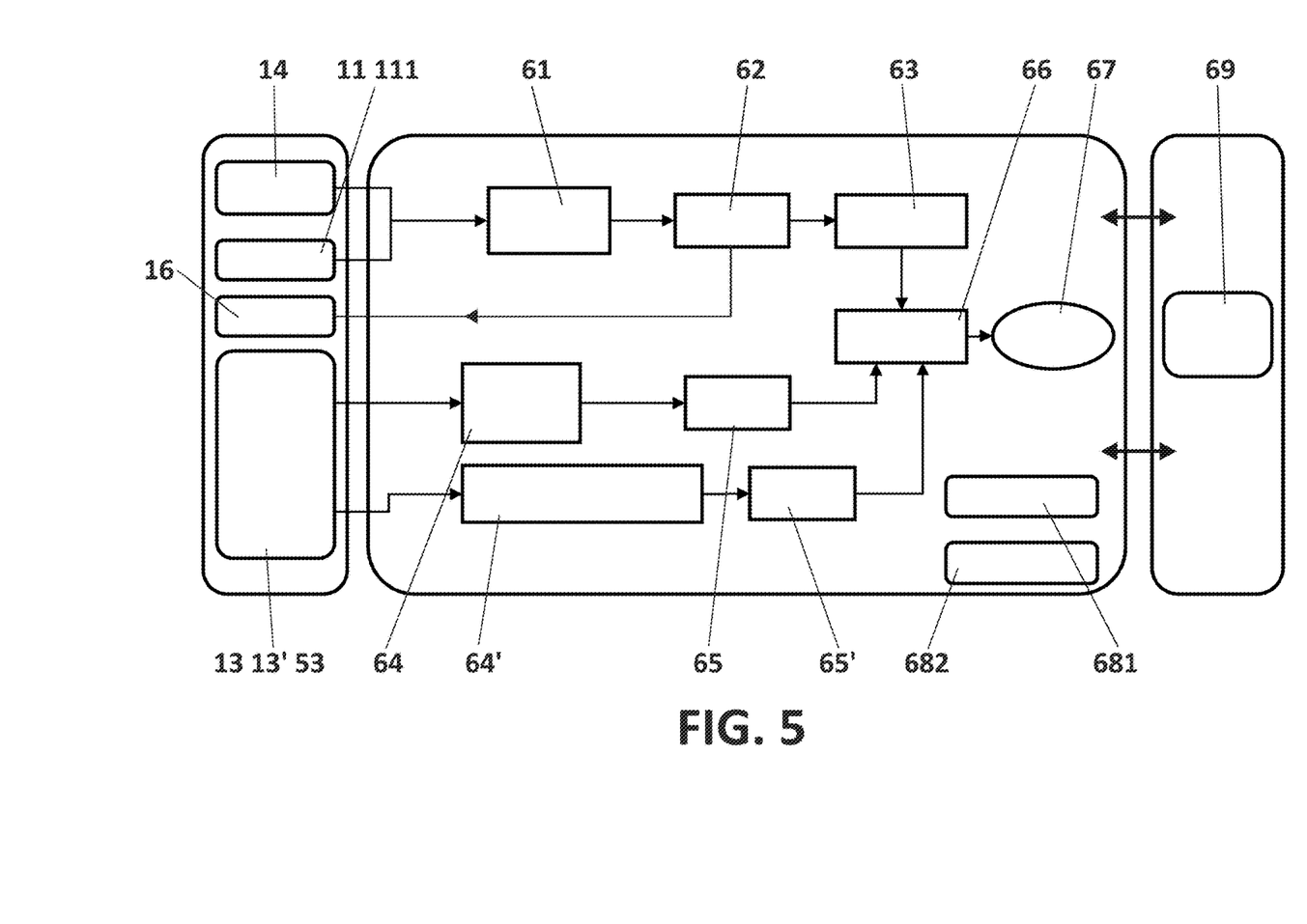
FIG. 5 shows the block modules of the system and method according to the invention.

FIG. 5 shows the block modules of the system and method according to different embodiments of the invention. On the left, the blocks corresponding to the hardware components are shown (plantar pressure distribution (also named baropodometric) system 13 53 or alternatively force/stabilometric platforms 13' or equipment which combines both baropodometric and stabilometric technologies, wearable module 11, reference module 14, and optionally a sensor actuator 16 (for example a servo motor). In the middle, the blocks corresponding to the software components, in charge of processing the information received from the hardware components, thus estimating a stability index 67. Also additional blocks for system configuration 681 and/or data management 682 are included. On the right, a block representing the graphical user interface 69 which enables the user to interact with the system (e.g. data visualization, assessment, training games, etc.). The different embodiments introduced in FIG. 5 are explained next.

Figure 1:
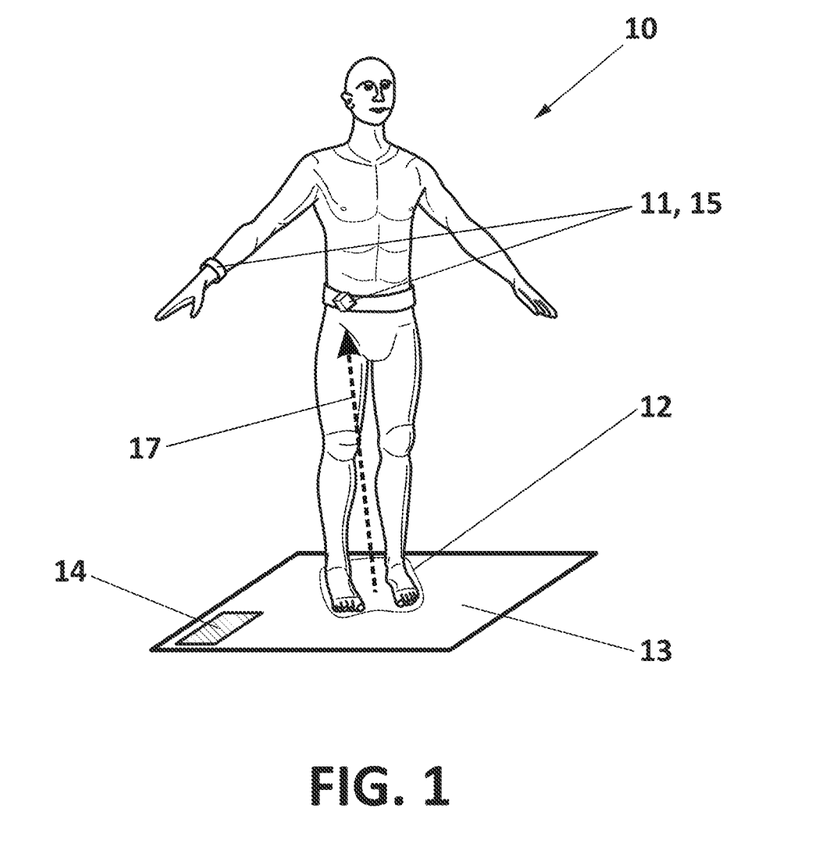
FIG. 1 shows a system according to a first embodiment of the invention.

FIG. 1 shows a system 10 according to a first embodiment of the invention. This system enables to carry out the inventive method. This first embodiment refers to a system for being used to assess and train people during tasks that take place in a limited space where walking is not possible (referred to as "non-nomad"). In this embodiment, the user is allowed to make any activity or motion within a specific platform or surface, that is to say, without leaving that platform or surface. In other words, the user can make dynamic standing activities, such as bending down, on leg balance, and crouching for example. In another embodiment (referred to as "semi-nomad"), the platform covers a larger area and is, therefore, suitable for short walking.

The system 10 comprises three main parts: at least one reference module 14, at least one wearable device 11 and at least one platform 13. It can additional have a remote computer, not illustrated in FIG. 1. The computer can be a laptop and runs the main software application which enables to carry out the method of the invention.

The at least one reference signal provided by a reference module 14 is used. Each reference module 14 is located at a fixed and known position with a determined orientation. The reference signal can be of one or several physical characteristics such as electromagnetic waves, (ultra) sounds, light, etc. In the particular implementation of FIG. 1 only one reference module 14 is shown.

In a preferred embodiment, the reference module 14 is located outside the platform 13, for example on the floor or on a wall. In an alternative embodiment, the reference system 14 is superimposed or embedded on the platform 13, as illustrated in FIG. 1.

Figure 2:
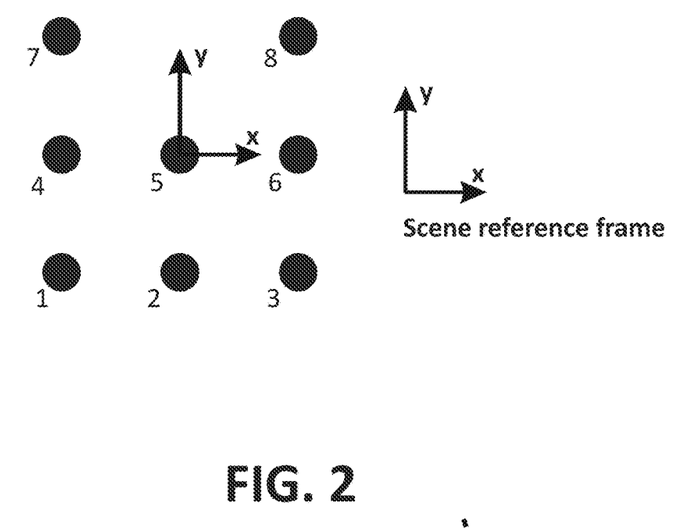
FIG. 2 represents a schematic view of a pattern of eight elements, including the reordering function.

In a preferred embodiment the reference signal uses infrared light. The reference module 14 providing the reference signal comprises a visual pattern formed by a plurality of infrared sources. In a particular embodiment, it is formed by a plurality of high intensity infrared LEDs mounted on a planar surface. In a non-limiting example, there are eight high intensity infrared LEDs (e.g. conventional elements for example VSMF4720) of dimensions 2.8×3.5×1.75 mm. The elements or items of the pattern 14 can be separated from each other by a distance which can vary between 2 and 20 cm. Power is supplied to the elements of the pattern by either a conventional power supply unit, such as a wall adapter or a battery. FIG. 2 represents a schematic view of a pattern of eight elements. Alternatively, the visual pattern 14 can be any visual information (e.g. picture, reflective markers, or natural environment) capable of serving as a reference.

The reference module 14 (for example visual pattern) serves as a reference in the subsequent determination of the position of the wearable devices 11. Since the position of this reference module 14 and the platform 13 are known and constant, any position of features estimated from the platform (e.g. Base of Support 12, ground reaction force & Centre of Pressure 17) is also known (see $^{scene}T_{plate}$ later).

The at least one wearable device 11 (also referred to as wearable sensor 11) relates its position and orientation with respect to the platform(s) 13 by means of the reference signals provided by the reference module 14. The ultimate goal is to relate the position and orientation the Human Center of Mass to information extracted from the platform (e.g. Base of Support and/or Centre of Pressure). Therefore the number and location of wearable devices 11 must be taken into account especially when considering both system usability and CoM estimation accuracy issues. In general, the more wearable sensors used, the more accurate the CoM position estimation will be.

In a particular embodiment, shown in FIG. 1, there are two wearable devices or sensors 11: one attached to the user's trunk and one attached to the user's arm. In this particular embodiment, they are respectively fixed to a belt and bracelet worn by the user.

As an example, in an embodiment requiring a minimal sensor configuration, a single wearable device might be used. In this case it is preferable to locate it as close as possible to the Center of Mass (CoM) of its wearer: meaning attached to the user's chest or trunk. It can be attached by means of a belt or by means of any conventional alternative fixing or attaching means.

Figure 3:
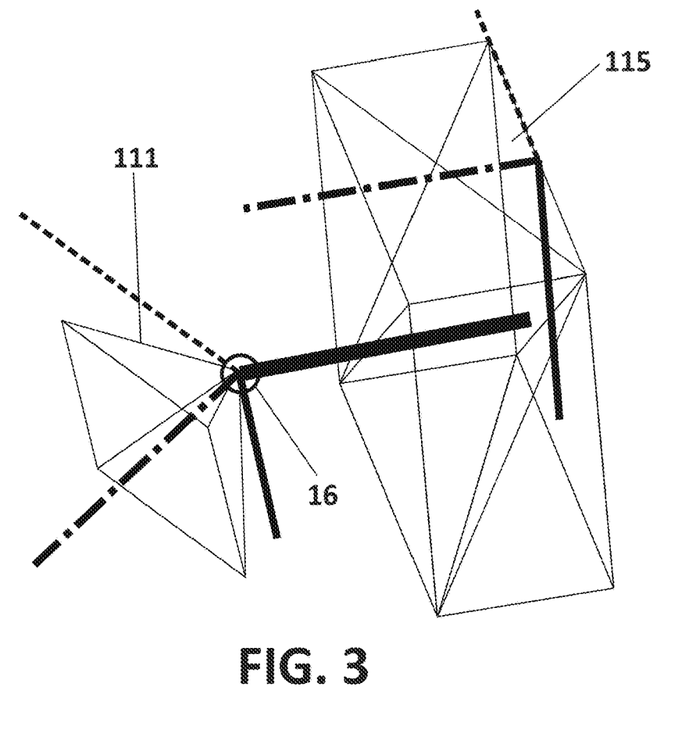
FIG. 3 shows an example of a camera mounted into a box.

In a preferred embodiment, the at least one wearable device 11 is made of a miniaturized (possibly low-cost) camera 11 which is mounted into a box 15 and connected to a processor board (not illustrated) which, in use, is configured for extracting image features in order to estimate the position of the camera based on techniques such as SLAM, or planar Homography (Direct Linear Transform (DLT) algorithm) FIG. 3 shows an example of a camera 111 (and its reference frame) mounted into a box 115 (wherein its reference frame is also outlined). The wearable device or sensor 11 is preferably actuated by actuating means 16, such as a servo motor, schematically shown in FIGS. 3 and 5. For example, the orientation of the sensor connected to the body is actuated by at least one servo motor. The at least one servo motor preferably has two DoF (degrees of freedom). The actuating means 16 is used to warranty that the wearable sensor is oriented towards the reference system.

As presented earlier, the preferred embodiment of the reference module 14 uses an infrared pattern, therefore the camera 11 embedded into the wearable device is preferably configured for capturing only the infrared light. For these reasons, the camera 11 preferably comprises a light filter which captures only light information in a certain wavelength range. More preferably, the light filter is an IR band-pass filter centered on 850 nm inserted in the mount of the camera between the lens and the image sensor.

Having an infrared visual pattern 14 and a band-pass IR filter in the camera, the images recorded are almost binary images (white spots or blobs over a black background), and thus simplifying the image segmentation and therefore reducing image post-processing time.

In use, when the body segment where the wearable sensor 11 is attached to is performing an important rotation, it is possible that the wearable sensor(s) is getting less optimally oriented toward the reference signal (in the preferred embodiment it means that the visual pattern 14 is moving toward an edge of the image captured by the camera). In order not to lose the reception of the reference signal two non-exclusive solutions have been implemented. First, the selection of an optical lens (of the camera 11) that provides a good compromise between the field of view (FOV) and pose estimation accuracy. Second, the use of a lightweight tilt and pan set actuated by micro servos. When the reference signal (e.g. the visual pattern) is about to get outside the field of view of the receiver (e.g. the camera), the servo motors are actuated to better orientate the receiver toward the reference signal.

Optionally, an Inertial Measurement Unit (IMU) can be embedded into the wearable sensor 11 in order to improve the sensor pose estimation in terms of accuracy but also sampling rate. IMU are composed of 3D accelerometers and gyroscope measuring both the linear acceleration ($m.s^{-2}$) and angular velocity ($rad.s^{-1}$) with a sample rate around 1000 Hz. Compared to the 30 Hz of regular (low cost) camera, the IMU provides measurements and then estimation of the wearable position and orientation between two captured images. In practice we use an extended Kalman filter (EKF) to fuse the vision and inertial measurement [Hol 2011]. The EKF handles the different sample rates. It runs at the high data rate of the IMU and the vision updates are only performed when a new image is available. The IMU gives very accurate short-term predictions of the sensor pose while vision based estimation provides absolute pose estimation (allowing IMU drift cancellation).

The at least one wearable sensor(s) 11 preferably embeds a preferably low cost, low power and small-sized processing board which acquires and sends images or features to a computer (not illustrated) preferably wirelessly.

The at least one platform 13 comprises a plurality of sensors (not illustrated in FIG. 1) for measuring the forces/pressures below the user's feet. In the embodiment shown in FIG. 1 there is one platform 13. It is preferably a plantar pressure distribution system (also referred to as PPD system and also named baropodometric device). In a preferred embodiment, it comprises an array of M×M sensors (at least a total of 3 sensors) distributed on a certain area (within the dimensions of the platform 13). Each one of these sensors measures the force and or momentum applied on it. In a particular embodiment, in which a conventional PPD system is used, the PPD system 13 comprises 1024 thin-film force sensors (32×32) for a total dimension of 50×50 cm. These devices measure the pressure distribution over the entire plantar surface (matrix type).

In an alternative embodiment, not shown in the figures, instead of using a plantar pressure distribution system, which permits to calculate a base of support 12, a force plate (or stabilometric platform) is used and allows estimating the Center of Pressure (CoP) and/or ground reaction force (GRF). By combining CoP (and/or GRF) and Center of Mass (CoM), a stability index can be obtained. In other words, the force plate or stabilometric system provides an alternative way of estimating the postural stability of a user.

As a remark, there are systems that combine both baropodometric and stabilometric measurements. There are also sensorized platforms as described above which are not immobile but that can move (e.g. change of orientation).

Figure 4:
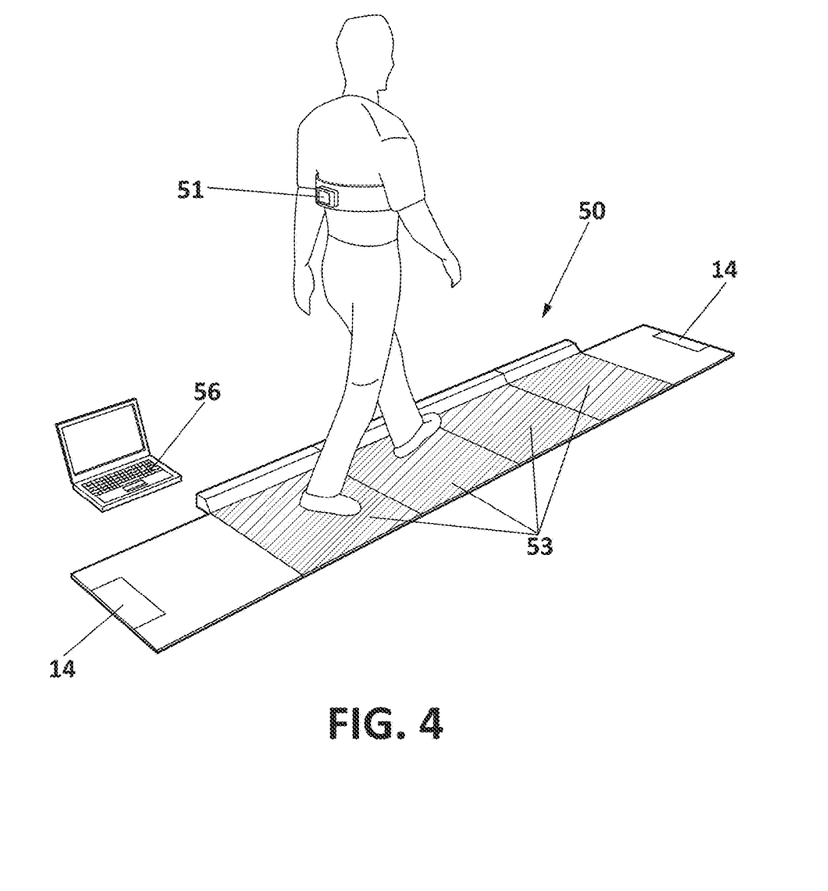
FIG. 4 shows a system according to an alternative embodiment of the invention.

FIG. 4 shows a system 50 according to a second embodiment of the invention. This system also enables to carry out the inventive method. This second embodiment refers to a system for being used with a moving person (also referred to as "semi-nomad"), that is to say, the measurements are taken while the person under examination walks along a sensorised walkway (frontwards or backwards), or a treadmill or similar device. The system either comprises a single platform 53 which is long enough so as to allow a person to walk on it, or it comprises a plurality of platforms 53 preferably disposed in a row. This system differs from the one described in the embodiment referring to FIG. 1 in that, while in FIG. 1 the system 10 could work with one reference module 14, the system 50 needs at least two reference modules 54 (such as visual patterns) to cover both the "go" and the "return" walks. The system 50 also comprises some hardware components, which are described next, for capturing sensory inputs which are processed. Like in the first embodiment, from the processed signals it is possible to estimate a stability index. This second embodiment represents an approach which can be considered as a natural extension of the first one ("non-nomad approach"). It is an interesting new functionality, as walking postural control mechanisms and skills are different from the ones derived from the limited possibilities of the first embodiment. Like in the first embodiment, the platform or platforms 53 can be pressure distribution systems (PPD systems), baropodometric devices or force platforms.

The system 50 also comprises at least one wearable device 51 (sensor device) attached to the user's body, such as a camera, which is similar to the camera 11 of the former embodiment and also preferably placed into a box and attached the chest of the user. The at least two reference modules 54 are located within the sensor device 51 field of view. Like in the system of FIG. 1, the reference modules 54 are preferably infrared visual patterns. There are as many visual patterns as necessary for fulfilling the requirement that always one visual pattern is within the field of view of the wearable device 51. In a possible embodiment, a first visual pattern 54 is located at a first end of the sensorized walkway comprising the platform or platforms 53 and a second visual pattern 55 is located at a second end (opposite to the first end) of walkway. This allows taking measurements while the person walks back and forth. Alternatively, the system 50 can have one or more visual patterns located along one or both sides of the walkway.

FIG. 4 also shows the computer 56 which processes the image features provided by the processor board associated to the wearable device 51. The system 50 also preferably comprises a graphical user interface (GUI) not shown in FIG. 4, which enables system configuration, data visualization and training games. It is similar to the one described in relation to the system 10 of FIG. 1.

Next, methods are described for assessing and training the postural stability of a Human body based on complementary information (such as CoM, CoP, BoS) provided by at least two measurement systems that can relate their positions through a reference signal.

As a generic description based on the scheme of FIG. 5, a Stability Index 67 is derived from the relative position and orientation of CoM and from either the BoS or CoP:

1) CoM position and orientation is estimated 63 from the wearable sensors position and orientation 62. The wearable sensor position and orientation are estimated 61 with respect to the reference module 14.

2) BoS is estimated from the plantar distribution system 13 when available.

3) CoP is estimated from the platform 13 when available.

A Stability Index (SI) 67 is obtained by combining the position and orientation of the wearable sensor(s) 11 111 1011 with the Center of Pressure (CoP) and/or the Base of Support (BoS) are/or derived features from them. SI can be expressed as follow:

SI=$f$(wearable sensor(s) position and orientation, BoS, CoP, GRF, derived features)

The function $f$ allows to: (a) combine the information using different techniques, (b) give different importance (weight) to the various inputs, (c) normalize data according to user/patient characteristics. In particular, one or more of said various inputs can be assigned a weight equal to zero, what means that said one or more inputs are not included in the calculation of the SI. However, the information derived from the position and orientation of the wearable sensor(s) 11 111 1011 is always taken into account.

In the context of this invention, the center of pressure (CoP) is the point on a body where the total sum of a pressure field acts, causing a force and no moment about that point. The total force vector acting at the center of pressure is the value of the integrated vectorial pressure field. The ground reaction force (GRF) and center of pressure location produce equivalent force and moment on the body as the original pressure field. In postural control assessment, CoP is usually measured with a force platform (planar surface equipped with at least three force and moment transducers). The relevant CoP information is a 2D position (x, y) while its vertical component (z) remains constant.

In the context of this invention, the Base of Support (BoS) is defined as the possible range the centre of pressure (CoP) can cover in order to compensate or control movements of the CoM. In principle, the BoS is an area delimited by a perimeter defined by the position of a person's parts of the body (i.e. feet) that are in contact with a supporting surface. In other words, the BoS represent all the points (x, y) within said perimeter.

In the context of the present invention the Human Center of Mass (CoM) can be estimated from the position and orientation of the wearable sensor(s). CoM is the unique point where the weighted relative position of the distributed mass sums to zero. In other words, it is the point in an extended body at which the mass of the body may be considered to be concentrated and at which external forces may be considered to be applied. The CoM is represented by a 3D point (x, y, z).

The method of the invention is described using a preferred embodiment where the wearable module is made of a camera filtering out the visible light and the visual pattern is made of small infrared emitting LEDs. In one embodiment, a platform providing plantar pressure distribution is used. In another embodiment, a force plate is used.

Publications have demonstrated the usefulness of both CoM and foot placement to assess human postural stability [Pai 1997]. We describe now in the inventive method how (i) CoM and foot placement (or BoS) are measured, (ii) how these two positions are related and (iii) how they are combined into a stability index, later on used for assessment or training purposes.

As an illustrative example, in an embodiment requiring a minimal sensor configuration, a single wearable device is used and attached to the chest. A method is described, that allows the estimation of the wearable sensor position and orientation. This is then used to estimate the CoM position 63 where, in a possible embodiment and as a first approach, a series of homogeneous spatial transformations are applied. For that purpose a set of coordinate systems is defined, as well as homogenous coordinate transformations between these coordinated systems. A homogeneous coordinate transformation matrix is represented as bold letter T.

The coordinate system from which the transformation is applied is represented by a lower case subscript which appears after the matrix symbol. The resulting coordinate system is denoted by lower case superscript which precedes the symbol. Vectors will be illustrated with capital letter preceded by a lower case superscript which represents the coordinate system in which they are expressed. For example ($^{scene}$COM) is the Center of Mass vector (x,y,z) expressed in the scene coordinates.

Figure 8:
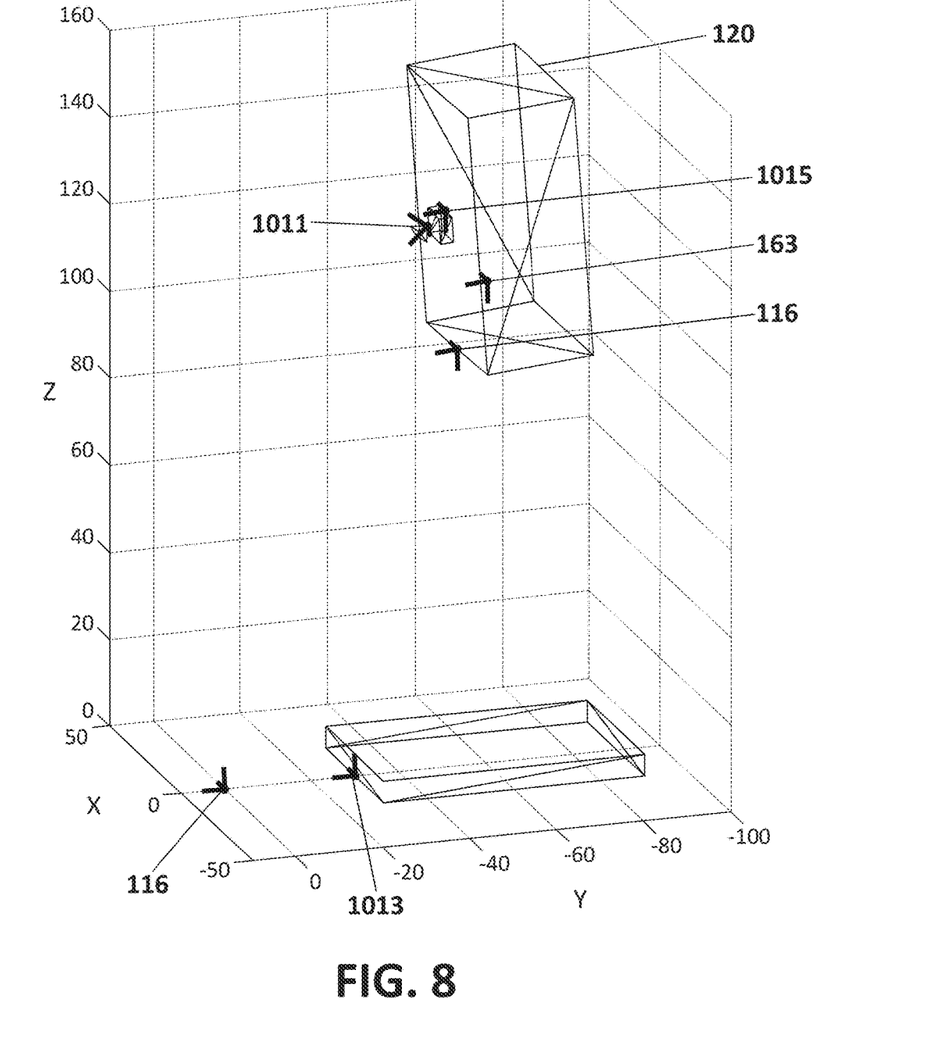
FIG. 8 shows a non-limiting example of the various frame coordinates used in one embodiment of the invention.

The various reference frames are illustrated on FIG. 8. The concerned transformations are the following:

$^{scene}T_{cam}$: from Camera (1011) to Scene reference frame (1014)

$^{scene}T_{box}$: from Box Point of Interest (1015) to Camera (1011)

$^{scene}T_{sac}$: from Human Sacrum (116) to Box Point of Interest (1015)

$^{scene}T_{com}$: from Human CoM (163) to Human Sacrum (116)

$^{scene}T_{plat}$: from Platform (1013) to Scene reference frame (1014)

The final goal is to estimate the CoM position and orientation expressed in the scene reference frame 1014 (($^{scene}$)COM). It can be expressed in the following manner:

$$^{scene}COM = (^{scene}T_{cam} * {}^{scene}T_{box} * {}^{scene}T_{sac} * {}^{scene}T_{com})$$
$$^{com}COM \qquad \text{Equation 1}$$

Figure 9A:
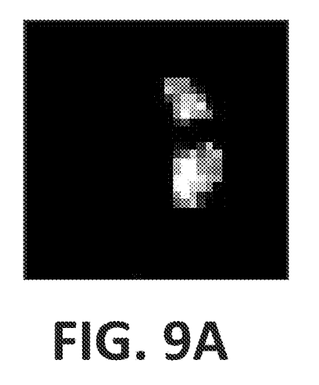
FIGS. 9A and 9B represent an example of the acquired data for calculating a base of support.

From the above equation most transformation matrices are known:

$^{cam}T_{box}$: Known but can vary over time. Based on the mechanical design of the wearable sensor 1011 and the known orientation of the servo motors as shown in FIG. 9A, which shows the rigid transformation applied relating the position and orientation of the origin of the camera 1011 with respect to a point of interest of the box 1015.

$^{box}T_{sac}$: Known and fixed. Wearable sensors 1011 are positioned at a known location with respect to the sacrum 116 of the subject.

$^{sac}T_{com}$: Model learned from motion analysis data sets.

$^{scene}T_{plat}$: Known and fixed position of the platform 1013 with respect to the reference module 1014. If needed, a wearable sensor (14) can also be placed on the platform in order to measure its position with respect to the reference module.

Then only $^{scene}T_{cam}$ is unknown and has to be estimated at every moment.

Estimating the position and orientation of the camera 1011 in the scene coordinates ($^{scene}T_{cam}$) requires a model of the image formation process. Such a model is expressed as a composition of the intrinsic (K), extrinsic camera ($^{scene}T_{cam}$) parameters and projection matrix $P_0$ of the camera leading to:

$$^{cam}POI = K \cdot P_0 * {}^{cam}T_{scene} * {}^{scene}POI \qquad \text{Equation 2}$$

$$P_0 = \begin{pmatrix} 1 & 0 & 0 & 0 \\ 0 & 1 & 0 & 0 \\ 0 & 0 & \frac{1}{f} & 0 \end{pmatrix}$$

-continued $$K = \begin{pmatrix} k_x & -k_x \cos\theta & C_x \\ 0 & k_y \sin\theta & C_y \\ 0 & 0 & 1 \end{pmatrix}$$

where, $^{scene}POI \in R^3$, are Point of Interests (POIs) expressed in the scene reference frame (e.g. the visual pattern (14, 1014)) and, $^{cam}POI \in R^2$, the same point but on the image of the camera. $k_x$ and $k_y$ are pixel dimensions. $C_x$ and $C_y$ are the coordinates of the optical center of the image, and θ the pixel angle (generally π/2).

In order to estimate $^{cam}T_{scene}$ from Equation 2, the strategy is to have a known pattern (composed of point or any 3d features, known in term of dimension, location . . . ), and apply a process to extract from the image the projection of this pattern. The example we provide now is an illustration of how it can be done: vector $^{scene}POI$ is known and corresponds to the pattern described in FIG. 2. Vector $^{cam}POI$ is estimated from the image provided by the camera pointing toward the reference pattern (see FIG. 9A). Among other possibilities it can be achieved by applying the following process (outlined in FIG. 6).

Figure 6:
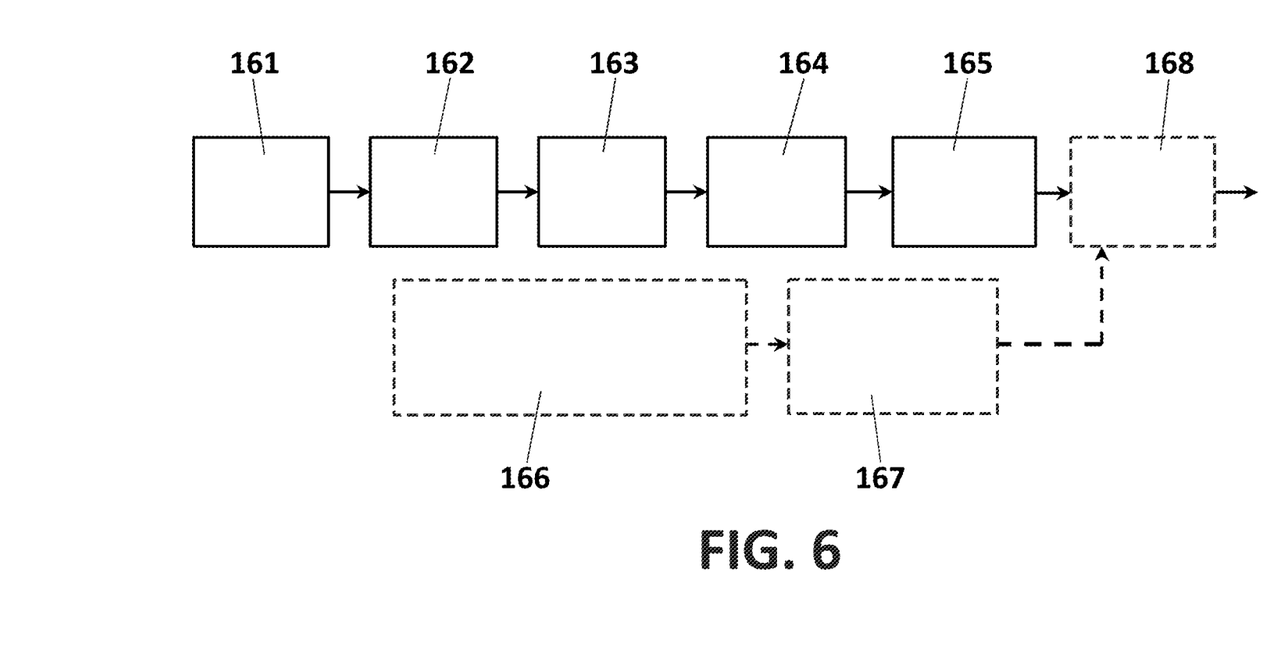
FIG. 6 shows a block diagram describing the process to estimate the position and orientation of a wearable module.

As outlined in FIG. 6, from the images provided by the camera 11 1011 at a predefined rate (for example, 30 pictures per second or more) a first preprocessing 161 is applied, transforming the input image (usually composed of three channels when considering color images or onl channel when considering gray-level images) into a single one (e.g. by keeping one channel or combining several ones). This is preferably done in order to decrease the processing time while keeping most of the information. A thresholding process is further and preferably applied for image binarisation. A compromise must be considered: if the threshold applied is very low, too much noise can be introduced in the image. On the other hand, if it is very high, it can cause information losses.

Figure 7:
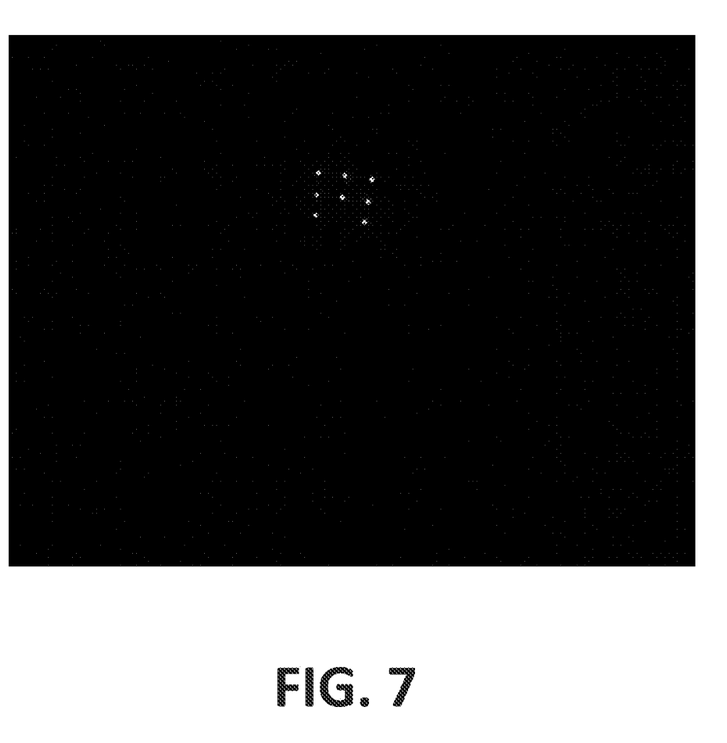
FIG. 7 shows an illustration of the type of image recorded by the camera. Height white PoI corresponding to the height infrared LEDs of the visual pattern.

The binary image extracted should only contain points (PoI) corresponding to the height infrared LEDs of the visual pattern (FIG. 7).

It might happen that additional elements are still present in the image. It is therefore preferable to detect 162 the region of interest (RoI), being the area where a concentration of points is expected. First a closing operation is applied to the whole image with an appropriate number of steps to assure that the different image points get merged. Among several potential RoIs, the RoI selected is the one that matches constraint related to its size and shape and temporal consistency (meaning that Region of Interests at time t and t+1 frame are spatially close).

Once the RoI is selected it is then possible to detect 163 the location, in the image, of the point of interest (PoI). When PoI are localised 163, they are reordered 164 (see for example FIG. 2).

Once the PoIs have been reordered 164, the camera pose ($^{scene}T_{cam}$) is estimated 165 using a minimization process (extrinsic parameters estimation). In this process, the vector $^{scene}POI$ is re-projected onto the camera reference frame ($_{reprojected}{}^{Cam}POI$) and the pixel re-projection error ($_{reprojected}{}^{Cam}POI - _{acquired}{}^{Cam}POI$) is minimized in the least squares sense over the intrinsic and extrinsic camera parameters. Then each time $^{scene}T_{cam}$ is estimated a new position of the CoM is computed according to Equation 1.

In parallel to the camera position and orientation estimation 165, complementary measurements 166 can be performed inside the wearable device in order to estimate its relative motion 167 (e.g. incremental translation and rotation) and therefore refine the camera position and orientation estimation 165 by fusing both sources of information 168.

In a possible embodiment the following measurements are additionally taken: the sensor acceleration and/or the sensor angular velocity and/or the magnetic orientation of the sensor. If these additional measurements are taken, the estimation of the relative position of the sensor 11 111 1011 can be refined 168 as follows: First, the acceleration and/or angular velocity and/or magnetic orientation of the sensor is acquired 166; then the sensor relative translation and orientation is estimated 167; finally the estimation of the sensor position and orientation is refined 168 by combining the initial estimation 165 with the additional information available.

The output of the minimization process (extrinsic parameters estimation) 165 (168 if available) is $^{scene}T_{cam^*}$ From $^{scene}T_{cam^*}{}^{scene}COM$ is then computed using the Equation 1. One innovation of this invention is to relate the position of the Human CoM ($^{scene}COM$) or other body parts to foot related information (e.g. BoS, CoP).

For that purpose and as represented in the block diagram of FIG. 5, if a plantar pressure distribution system or a baropodometric system 13 53 is used, a base of support BoS can be calculated (blocks 64, 65). Conventional platforms provide, through a software API (e.g. a dll file), real-time access to the data. In this case it is a matrix ($\in R^2$) in which each cell contains the vertical force/pressure value of the corresponding sensors. The higher the value the more force is applied on the sensor.

Figure 9B:
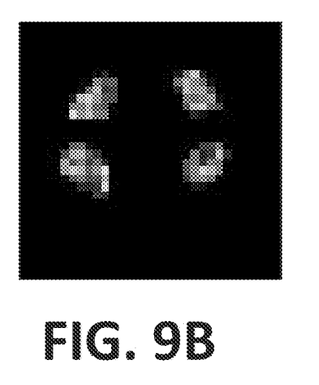

FIGS. 9A and 9B represent an example of the acquired data for respectively one foot and two feet. In a particular implementation, the information is stored in a 32×32 matrix.

Figure 10A:
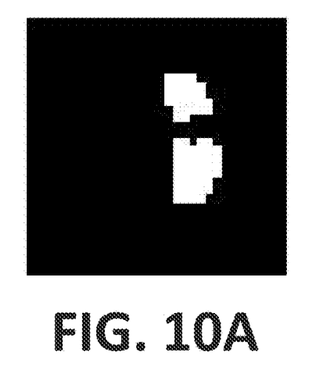
FIGS. 10A and 10B represent an example of a binarised image for calculating a base of support.
Figure 10B:
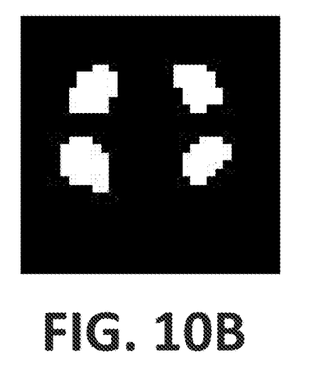

Next the extraction of the BoS (stage 65) is described: Once acquired this pressure data matrix, a binarisation function is applied with a certain threshold. The threshold value is defined in order to discard sensor noise (pressure below threshold is re-assigned to zero) and assign a value of one when a real pressure is applied. FIGS. 10A and 10B represent an example of the binarised image for respectively one foot and two feet.

Figure 11A:
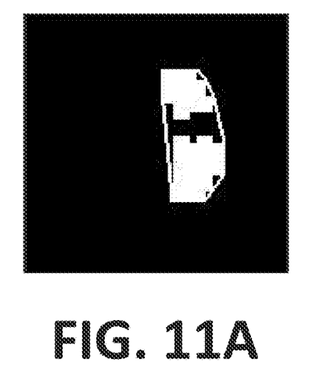
FIGS. 11A and 11B represent an example of the convex hull obtained from the binarised image of FIGS. 10A and 10B.
Figure 11B:
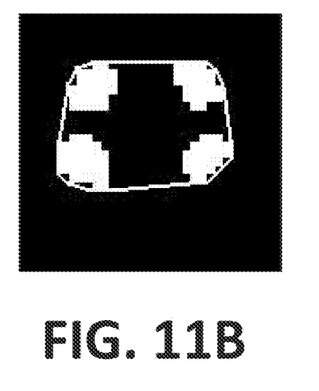

Once the image is binary, a function for calculating the convex hull of the points is executed. A convex hull of a set X of points in the Euclidean plane is the smallest convex set that contains X. The BoS is obtained from the points ($^{plat}BOS$) describing the convex hull (stage 65). FIGS. 11A and 11B represent an example of the convex hull obtained from the binarised image. Knowing the physical dimension of the sensor cell, the position of BoS points ($^{plat}BOS$) are converted into a metric dimension (e.g meters) and are expressed in the reference frame of the platform. Finally, the sequence of points is expressed in the scene reference frame by applying the following transformation:

$^{scene}BOS = {}^{scene}T_{plate} * {}^{plate}BOS$

Note that from the plantar pressure distribution matrix is it possible to extract a so called Centre of Force (CoF) defined as the barycentric coordinate considering that each sensor i has a spatial position (xi, yi) and pressure value Pi:

$$^{plat}COF = \begin{pmatrix} \sum_{i=1}^{n} x_i * \dfrac{P_i}{P_{tot}} \\ \sum_{i=1}^{n} y_i * \dfrac{P_i}{P_{tot}} \end{pmatrix}$$

With $P_{tot} = \sum_{i=1}^{n} P_i$

Similarly $^{scene}COF = {}^{scene}T_{plat} * {}^{plat}COF$

If, alternatively, a force plate or a stabilometric system 13' is used, the system deliverers 6 DoF measurements: 3D ground reaction forces $$^{plat}GRF = \begin{pmatrix} F_x \\ F_y \\ F_z \end{pmatrix}$$

and 3D moments $$^{plat}M = \begin{pmatrix} M_x \\ M_y \\ M_z \end{pmatrix}.$$

From these measurements the Center of Pressure (CoP) can be calculated (64'):

$$^{plat}COP = \begin{pmatrix} -\dfrac{M_y}{F_z} \\ \dfrac{M_x}{F_z} \\ 0 \end{pmatrix}$$

and transformed into the scene reference frame:

$$^{scene}COP = {}^{scene}T_{plat} \cdot {}^{plat}COP$$

$$^{scene}GRF = {}^{scene}T_{plat} \cdot {}^{plat}GRF$$

At stage 66 in FIG. 5, all measurements are expressed in the scene reference frame: $^{scene}COM$; $^{scene}BOS$; $^{scene}COF$; $^{scene}COP$; $^{scene}GRF$. It is therefore possible to analyse 66 the relative positions and evolution of these human postural stability descriptors and create a stability Index 67. It is important to note again that depending of the platform used one may have access to $^{scene}BOS$ only or $^{scene}COP$ only or both. This is why SI is expressed as follows:

SI=f(wearable sensor(s) position and orientation, BoS, CoP, GRF, derived features)

Where function $f$ allows to: (a) combine the information using different techniques, (b) give different importance (weight) to the various inputs, (c) normalize data according to user/patient characteristics. In particular, one or more of said various inputs can be assigned a weight equal to zero, what means that said one or more inputs are not included in the calculation of the SI. However, the information derived from the position and orientation of the wearable sensor(s) 11, 111, 1011 is always taken into account.

Figure 12:
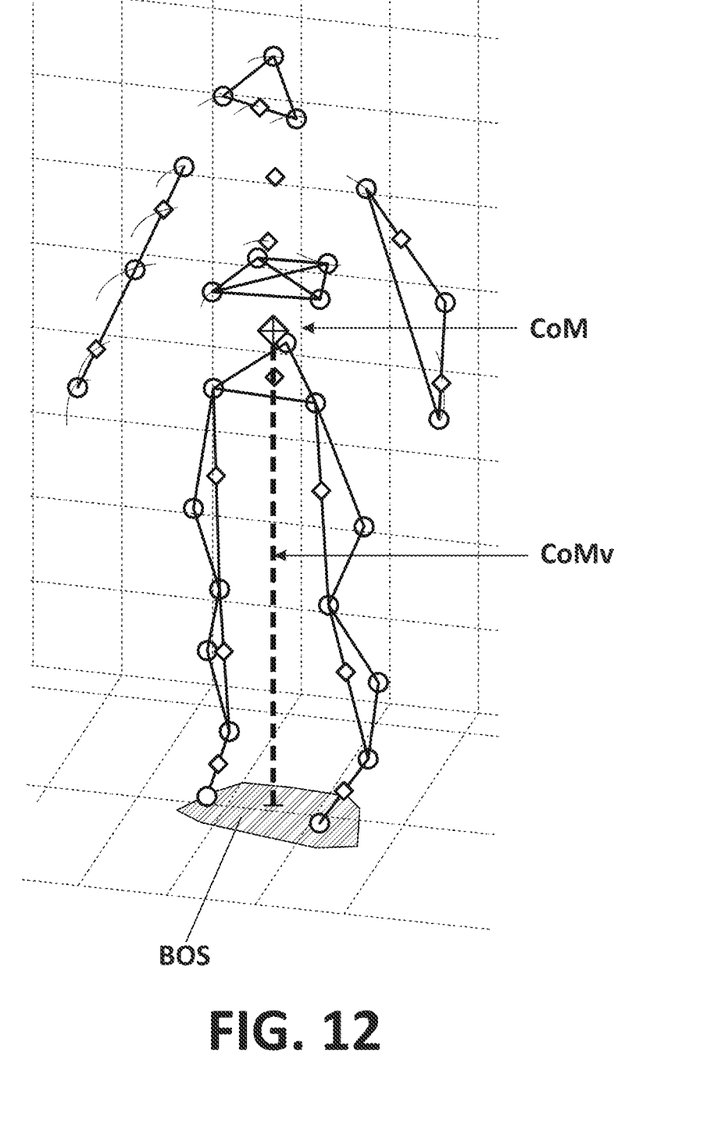
FIG. 12 shows an example of information used to estimate de SI.

As an example, if CoP is not available, the function f will assign zero to the weight associated with CoP (e.g., $\omega_{CoP}$). FIG. 12 shows an example of the information used to estimate de SI. In this case, the Center of Mass (CoM), the vertical projection of the Center of Mass (CoMv) and the Base of Support (BoS) are used.

Finally, the software and graphical user interface developed in this invention measures is used to (1) visualize instantaneously the measurements performed (e.g. position(s) of the wearable sensor(s), BoS, CoP, CoM, SI), (2) store/retrieve past recording, (3) guide the user (patient or professional) to run an assessment procedure, (4) engage the user into a training procedure (e.g. impose user foot placement and then request the user to follow a path with his/her Center of Mass, train CoM-CoP distance).

The stability index has many applications. For example, a doctor or clinician can evaluate from it the evolution of the patient or his/her lack of stability. For this purpose standard tests such as Romberg test, Functional Reach Test (FRT), Short Form Berg Balance Scale (SF-BBS), One-leg stance test, "Balance part" of the Tinetti Performance Oriented Mobility Assessment (POMA), Nudge Test, Postural Stress Test (PST) can be performed while using the system and method of the present invention. During the execution of the test, the clinician sees on graphical user interface the real-time evolution of relevant parameters (e.g. CoM, BoS, CoP, or derived features) and/or the stability index itself. After completion of the test, a report is generated with plots, tables of values, etc.

In addition, specific and new training sessions can also be prescribed using the possibility to jointly measure and feedback information about both CoM and foot placement. As an example, the software application will ask the user to position their feet at a specific location on the platform. The user sees on the GUI the targeted foot placement and tries to match these positions. A real-time visual feedback of the current feet positions is provided. When feet positions match the targets (normal, semi-tandem, tandem, others) the user is instructed not to move its feet and to move its CoM in order to follow a spiral path. The execution time is recorded as well as a score that is based on the number of time the CoM goes out of the path for example.

With the described system and method for assessing human postural stability based on the measurements and analysis of the simultaneous and relative evolution of at least two parameters of Human kinematics and/or kinetics, a stability index can be obtained from a parameter related to the center of mass (CoM) of a person and at least one parameter related to the relative position of the feet (e.g. Base of Support) or the Center of Pressure (CoP) of the person.

Please note that in this document, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

What is claimed is:

1. A system comprising:
   at least one platform configured for, in use, having a person on it, said platform comprising a plurality of sensors configured for capturing information of forces/pressures applied by the feet of the person or of the position of the person's feet;
   a computer processor configured for, from said captured information, respectively extracting either a center of pressure or the position of the feet;
   the system being characterized in that it further comprises:
   at least one reference module providing a reference signal, the at least one reference module being disposed at a fixed location with respect to said platform;

at least one sensor which, in use, is connected to the body of the person situated on said platform, the at least one sensor being worn by said person, the sensor worn by said person capturing the reference signal provided by the at least one reference module;

wherein the computer processor is further configured for:

extracting information from said at least one reference signal captured by the at least one sensor worn by said person, estimating from said reference signal captured by the at least one sensor worn by said person the position and orientation of said at least one sensor worn by said person with respect to the at least one reference module providing said reference signal, estimating the position and orientation of the body of said person from said estimated position and orientation of the at least one sensor in turn obtained from said at least one reference signal, and calculating a stability index from said position and orientation of the body of said person and from said extracted feet position or center of pressure.

2. The system of claim 1, wherein said at least one sensor connected to the body of the person situated on said platform comprises a camera and said at least one reference signal provided by said at least one reference module disposed at a fixed location with respect to said platform is a visual pattern.

3. The system of claim 2, wherein said at least one visual pattern is an infrared visual pattern and said at least one camera is configured to capture images in the infrared range of light.

4. The system of claim 1, wherein said platform is a plantar pressure distribution system or a force platform.

5. The system of claim 1, wherein said stability index is a function of the position and orientation of said at least one sensor connected to the body of the person situated on said platform and at least one of the following inputs: a base of support (BoS), a center of pressure (CoP), a ground reaction force (GRF) and one or more features derived from the base of support (BoS), the center of pressure (CoP) or the ground reaction force (GRF).

6. The system of claim 1, wherein said at least one sensor connected to the body of the person situated on said platform is adapted to be connected to the trunk of said person.

7. The system of claim 1, wherein said at least one sensor connected to the body of the person situated on said platform comprises at least one acceleration transducer for measuring the sensor acceleration or at least one angular velocity transducer for measuring the sensor angular velocity.

8. The system of claim 1, wherein said at least one reference module is placed on or outside said platform.

9. The system of claim 1, wherein the orientation of the at least one sensor connected to the body is actuated by at least one servo motor.

10. A method comprising the steps:

using a plurality of sensors located at a platform on which a person is situated, capturing information of the pressure applied by the feet of the person or of the position of the person's feet;

from said captured information, respectively extracting either a center of pressure or a feet position;

the method being characterized in that it comprises the steps of:

by means of at least one sensor connected to the body of the person situated on said platform, the at least one sensor being worn by said person, capturing at least one reference signal provided by at least one reference module disposed at a fixed location with respect to said platform;

extracting information from said at least one reference signal captured by the at least one sensor worn by said person;

from said reference signal captured by the at least one sensor worn by said person, estimating the position and orientation of said at least one sensor worn by said person with respect to the at least one reference module providing said reference signal;

from said estimated position and orientation of said at least one sensor in turn obtained from said at least one reference signal, estimating the position and orientation of the body of said person;

calculating a stability index from said position and orientation of the body of said person and from said extracted feet position or center of pressure.

11. The method of claim 10, wherein estimating the position and orientation of the body of said person is done as follows:

estimating the relative position of the sensor with respect to the at least one reference signal, said at least one reference signal being a visual pattern, and the orientation of the sensor;

extracting a point of interest, on the sensor, from said extracted information;

estimating a center of mass (CoM) of the person from said relative position and orientation of the sensor.

12. The method of either claim 10 or 11, further comprising the step of measuring a sensor acceleration and/or a sensor angular velocity and/or a magnetic orientation of the sensor.

13. The method of claim 12, wherein estimating the position and/or orientation of the at least one sensor is refined as follows:

acquiring the acceleration and/or angular velocity and/or magnetic orientation of the sensor;

estimating a sensor relative translation and orientation;

refining the estimation of the sensor position and orientation by combining an initial estimation with the sensor acceleration and/or the sensor angular velocity and/or the magnetic orientation of the sensor.

* * * * *